United States Patent [19]

Sjoquist et al.

[11] Patent Number: 5,247,939

[45] Date of Patent: Sep. 28, 1993

[54] DETECTION OF ELECTRODE/PATIENT MOTION AND FAST RESTORE LIMITS

[75] Inventors: Steven E. Sjoquist, Lynnwood; James W. Taylor, Seattle, both of Wash.

[73] Assignee: Physio-Control Corporation, Redmond, Wash.

[21] Appl. No.: 819,193

[22] Filed: Jan. 10, 1992

[51] Int. Cl.$^5$ ............................................. A61B 5/04
[52] U.S. Cl. ..................................... 128/697; 128/734
[58] Field of Search ............ 128/419 D, 734, 419 PT, 128/697, 696, 670, 908

[56] References Cited

U.S. PATENT DOCUMENTS

| | | | |
|---|---|---|---|
| 3,587,562 | 6/1971 | Williams | 128/723 |
| 3,608,543 | 9/1971 | Longini et al. | 128/419 D |
| 3,703,900 | 11/1972 | Holznagel | 128/419 P |
| 3,871,359 | 3/1975 | Pacela | 128/419 D |
| 4,305,400 | 12/1981 | Logan | 128/670 |
| 4,328,808 | 5/1982 | Charbonnier et al. | 128/419 D |
| 4,387,722 | 6/1983 | Kearns | 128/716 |
| 4,403,215 | 9/1983 | Hofmann et al. | 340/573 |
| 4,422,458 | 12/1983 | Kravath | 128/671 |
| 4,432,375 | 2/1984 | Angel et al. | 128/705 |
| 4,475,558 | 10/1984 | Brock | 128/710 |
| 4,506,678 | 3/1985 | Russell et al. | 128/723 |
| 4,574,810 | 3/1986 | Lerman | 128/419 D |
| 4,610,254 | 9/1986 | Morgan et al. | 128/419 D |
| 4,619,265 | 10/1986 | Morgan et al. | 128/419 D |
| 4,736,157 | 5/1988 | Betker et al. | 128/734 X |
| 4,785,812 | 11/1988 | Pihl et al. | 128/419 D |
| 4,840,177 | 6/1989 | Charbonnier et al. | 128/419 D |
| 4,870,341 | 9/1989 | Pihl et al. | 128/419 D X |
| 4,917,099 | 4/1990 | Stice | 128/696 |
| 4,919,145 | 4/1990 | Marriott | 128/723 |
| 4,993,423 | 2/1991 | Stice | 128/696 |
| 5,020,541 | 6/1991 | Marriott | 128/723 |
| 5,088,489 | 2/1992 | Lerman | 128/419 D |

OTHER PUBLICATIONS

"Thoracic Impedance of Human Subjects", Machin, J. W., Med & Biol. Eng. & Comput. Mar. 1978, No. 2-16, pp. 169-178.

Primary Examiner—Lee S. Cohen
Assistant Examiner—Jeffrey R. Jastrzab
Attorney, Agent, or Firm—Christensen, O'Connor, Johnson & Kindness

[57] ABSTRACT

A defibrillator/monitor (10) employing a motion detection circuit 18 and control and processing circuit (20) that cooperatively detect motion at a patient-electrode interface. In that regard, an impedance measurement circuit (24) produces an output indicative of the impedance of the interface. This output is then processed by a number of filter elements before being analyzed by a motion detection routine (52). The motion detection routine includes subroutines (62 and 64) that compare the impedance against distinct upper and lower limits and then monitor the time at which the signal is above and below the limits. Basically, motion is indicated if the signal undergoes relatively large variations for a short time, or smaller variations for a longer time. A third motion clear subroutine (66) is used to determine when motion is no longer detected. Finally, a similar scheme (102) is employed to quickly restore the various filter elements after saturation.

23 Claims, 12 Drawing Sheets

MOTION DETECTION ROUTINE 52

DETECTION OF ELECTRODE/PATIENT MOTION AND FAST RESTORE LIMITS

FIELD OF THE INVENTION

This invention relates generally to limits detection and, more particularly, to the detection of limits involved in the monitoring of electrode/patient motion and fast restore systems in medical instruments.

BACKGROUND OF THE INVENTION

A variety of medical instruments have been developed for use in monitoring and treating patients. Many of these instruments are designed to be electrically coupled to the patient via one or more electrodes. The electrodes receive electrical signals from, or transmit electrical energy to, some portion of the patient's body.

In that regard, a defibrillator/monitor typically includes two or more monitoring electrodes that receive electrical signals from the patient's heart. These signals are then commonly displayed by the monitor, allowing the attending physician to evaluate the heart's operation. In addition, a pair of defibrillation electrodes are used to transmit electrical energy from the defibrillator to the patient to, for example, terminate undesired fibrillation of the heart.

The monitoring and defibrillation electrodes used with the defibrillator/monitor are often applied externally to the patient's chest and/or limbs. As will be appreciated, the impedance of the electrodes, the transthoracic impedance of the patient, and the impedance of the electrode/patient interfaces, all influence the signals received by the monitor and the energy delivered to the patient. Typically, the electrodes are designed to reduce the influence of impedance on the instrument's operation as much as possible.

In that regard, external electrodes are made relatively large to reduce the impedance of the electrode/patient interface. Also, a conductive gel is often applied to the surface of each electrode before the electrode is attached to the patient to further limit the interface impedance. Despite such precautions, the impedance of the electrode/patient interface may still have undesired influences on the instrument's operation.

One of the most common problems involving electrode/patient impedance is related to motion. For example, with monitoring electrodes applied to a patient's chest, movement of the patient or the electrodes may disturb the patient/electrode interface. The resultant variations in interface impedance introduce corresponding variations in the electrical signals received at the monitor, independent of the operation of the heart. This "motion artifact" in the monitored signal can, in turn, cause the instrument or operator to erroneously interpret the condition of the heart.

Relative motion between the patient and defibrillation electrodes may similarly be of interest. For example, patient motion may indicate that the patient is conscious or is being moved by a health care provider. In either instance, it may be undesirable to discharge energy to the patient. Further, motion-induced variations in the impedance of the electrode/patient interface may result in corresponding variations in energy losses at the interface. Thus, the energy actually delivered to the patient to terminate fibrillation may differ considerably from that selected by the operator.

Prior art systems have been developed to address these limitations. In that regard, some systems monitor the impedance at the electrode/patient interface to determine when motion is occurring. In the event the monitored impedance suggests that motion is occurring, operation of the instrument is then inhibited.

By way of illustration, U.S. Pat. No. 4,919,145 (Marriott), assigned to Physio-Control, reviews a number of different techniques used to sense lead impedance and/or transthoracic impedance (TTI). In that regard, the background section of the Marriott patent indicates that a small DC signal can be applied to the leads, with the resulting DC voltage across the leads then being representative of impedance. Another approach described in the background section of the Marriott patent involves the application of a high-frequency, constant current signal to the leads. The Marriott patent then goes on to disclose an arrangement in which two carrier signals are used to detect a lead impedance related voltage and an impedance respiration related voltage.

U.S. Pat. No. 4,619,265 (Morgan et al.), also assigned to Physio-Control, discloses an arrangement in which a patient's TTI is evaluated to detect motion. More particularly, TTI signals are compared against some predetermined threshold level. If the last two measurements of TTI exceed the threshold, a display is generated prompting the operator to stop all motion. If motion is detected for more than fifteen seconds, the operator is also prompted to perform cardiopulmonary resuscitation.

With only one or two impedance measurements used to detect motion, temporary aberrations in the measurements due, for example, to noise are likely to influence the detection of motion. In that regard, noise in the measured impedance signal may cause the signal to be erroneously high or low at any given time. Although the resultant signal variations may average out over time, with only one or two measurements used, the measurements are likely to be inaccurate. As will be appreciated, it would be desirable to allow motion to be detected in a manner that is relatively free from the influence of noise.

As disclosed by Morgan et al., the use of limits detection plays an important role in conventional motion detection schemes, allowing an impedance measurement to be compared against some predetermined threshold level associated with motion. In accordance with the present invention, limits detection plays roles both in the processing of impedance data used in the detection of motion and in the processing of monitored cardiac signals used to evaluate the condition of the patient's heart.

In that regard, the signals used to monitor cardiac activity and electrode impedance are conventionally filtered by a preprocessing circuit prior to analysis. Filtering is performed to remove select portions of the signals, preserving only those portions that have a high information content. The removed portions may be attributable to, for example, some baseline signal contributor or noise.

The conventional filter circuits used often employ capacitive elements, as well as resistive and inductive elements. When the signal applied to such a filter circuit undergoes large deviations, the capacitors may become fully charged, rendering the filter inoperative until the charge stored on the capacitors has time to decay. As will be appreciated, it would be desirable to determine when the input to such a filter undergoes a large deviation, so that some form of corrective action can be taken to limit the inoperability of the filter circuit.

In view of the preceding comments, it would be desirable to develop a method of detecting limits associated with electrode/patient motion, free from the disruptive influence of, for example, noise. It would further be desirable to develop a method of detecting limits associated with the inoperability of filter circuits conventionally used in medical instruments. To reduce the complexity of the overall processing performed by the instrument, it would further be desirable for the same general method to be used in detecting both types of limits.

SUMMARY OF THE INVENTION

In accordance with this invention, a method is disclosed of hysteretically detecting the limits of a physiological signal processed by a medical instrument. The method includes the steps of comparing the signal to a first range of values. An inside time, representative of the time during which the signal is within the range of values, is then stored along with an outside time, representative of the time during which the signal is outside the range of values. An inside action signal is produced when the inside time exceeds a first inside time limit and an outside action signal is produced when the outside time exceeds a first outside time limit. The preceding steps are then repeated for a second range of values, with the repetition of steps for the first and second ranges of values introducing a hysteretic aspect to the method.

In one application of interest, the method is used to detect relative motion between an electrode and a patient. The electrode is coupled to the patient and to a medical instrument which provides a signal related to the impedance of the electrode/patient interface. The method includes the step of comparing the signal to a first range of values. A first inside time, representative of the time during which the signal is within the first range of values, is then stored along with a first outside time, representative of the time during which the signal is outside the first range of values. The first inside and outside times are set to zero when the first inside time exceeds a first inside time limit. A motion detection output, indicative of relative motion between the electrode and the patient, is produced when the first outside time exceeds a first outside time limit.

In accordance with yet another aspect of the invention, a method of restoring a filter circuit used to process the physiological input to a medical instrument is disclosed. The method includes the step of comparing the signal to a first range of values. A first inside time, representative of the time during which the signal is within the first range of values, is stored along with a first outside time, representative of the time during which the signal is outside the first range of values. The first inside and outside times are set to zero when the first inside time exceeds a first inside time limit. A filter restoration output is produced when the first outside time exceeds a first outside time limit.

BRIEF DESCRIPTION OF THE DRAWINGS

The invention will generally be described in greater detail, by way of example, with reference to the accompanying drawings wherein.

DETAILED DESCRIPTION OF THE PREFERRED EMBODIMENT

Figure 1:
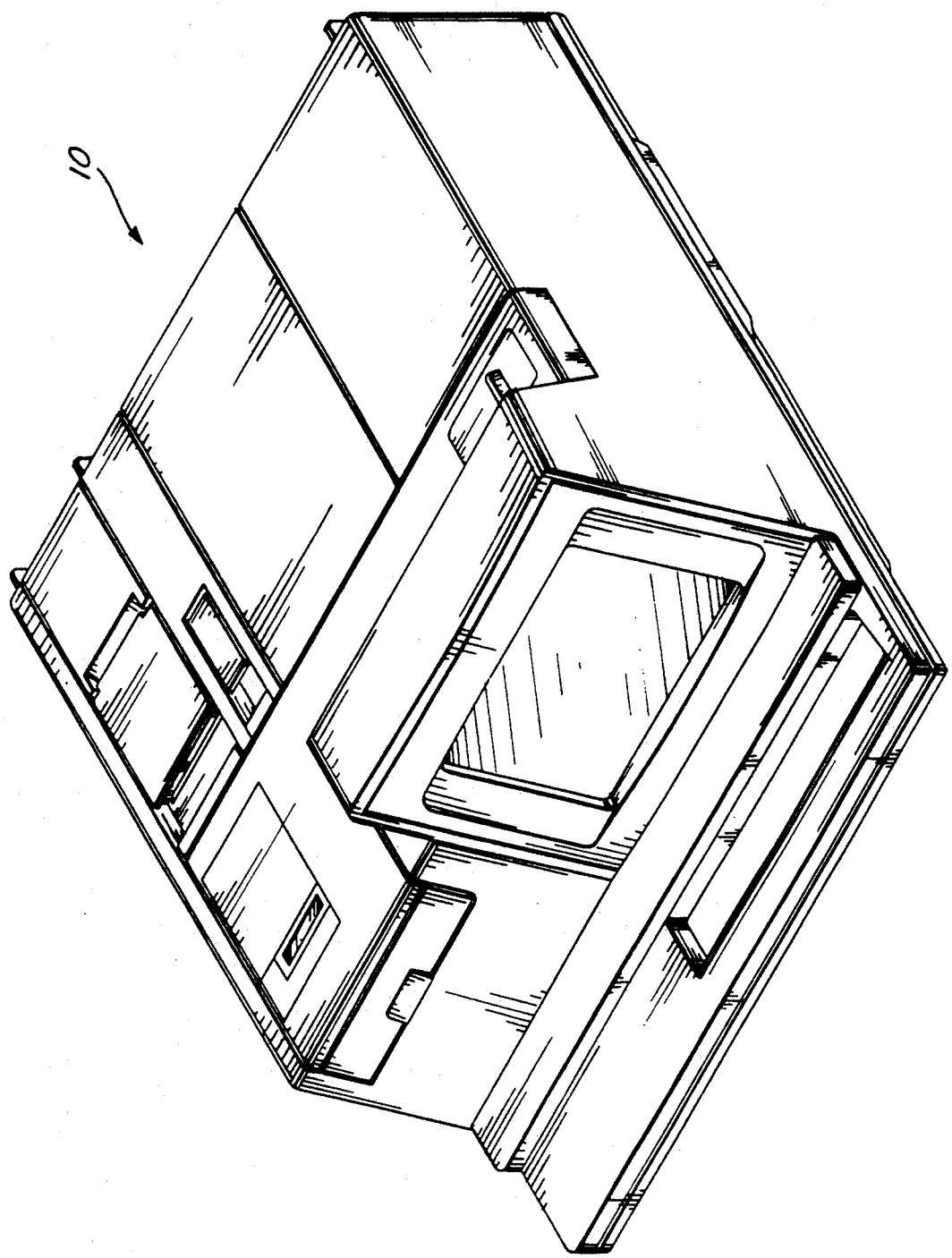
FIG. 1 is an illustration of a defibrillator/monitor constructed in accordance with the present invention and attachable to a patient via a pair of electrodes.

Referring now to FIG. 1, a defibrillator/monitor 10, constructed in accordance with this invention, is shown. The defibrillator/monitor 10 performs a variety of different functions. For example, the defibrillator/monitor 10 receives electrocardiographic (ECG) signals from the patient for use by an operator in monitoring the patient's heart. The defibrillator/monitor 10 is also conventionally designed to allow relatively large pulses of energy to be applied to the patient's heart to, for example, terminate fibrillation of the heart. Alternatively, smaller, periodic pulses of energy may be applied to stimulate a desired heart rate.

Each of these various functions requires the defibrillator/monitor 10 to be electrically coupled to the patient. Usually, three separate sets of monitoring, defibrillation, and pacing electrodes are employed. While conventional defibrillation and pacing electrode sets typically include two electrodes each, a variety of different monitoring electrode sets have been developed, including, for example, two, three, four, and ten electrodes.

Motion-induced impedance variations at the different electrode/patient interfaces may cause the ECG signals received from the patient to be misinterpreted by the defibrillator/monitor 10. Similarly, defibrillation and pacing pulses applied to the patient may be attenuated by the impedance fluctuations to an unknown degree. Further it may be undesirable to defibrillate a patient when motion is occurring. To overcome these limitations, the defibrillator/monitor 10 is designed to detect motion and, for example, to inhibit further operation until motion is no longer present.

In one preferred arrangement, the limits detection scheme implemented involves a hysteretic analysis that provides greater immunity from noise than conventional motion detection systems. The broad limits detection scheme also has applicability to the restoration of certain filtering circuits used in the detection of motion and the general processing of ECG signals.

Figure 2:
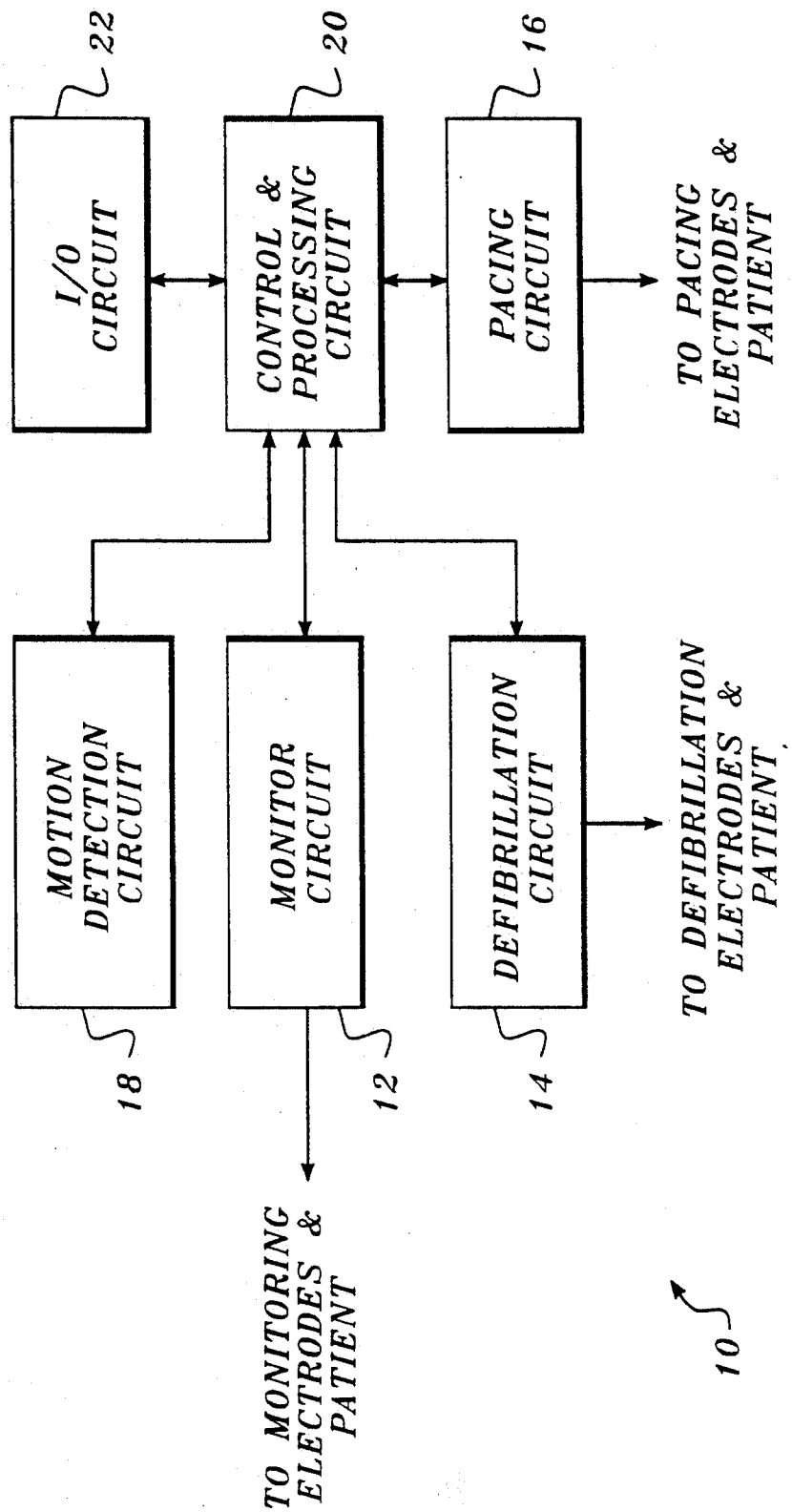
FIG. 2 is a block diagram of a defibrillator/monitor of the type shown in FIG. 1, illustrating the interrelationship of the various components of the instrument.

Turning now to a more detailed review of the construction of the defibrillator/monitor 10, reference is had to the block diagram of FIG. 2. As shown, the defibrillator/monitor 10 includes a monitoring circuit 12, defibrillation circuit 14, pacing circuit 16, and motion detection circuit 18, all regulated by a control and processing circuit 20. An input/output (I/O) circuit 22 allows the operator to apply inputs to circuit 20 and provides the operator with the various instrument outputs. With the exception of the motion detection circuit 18 and the related operation of the control and processing circuit 20, the various components of defibrillator/monitor 10 are conventional in nature and are only briefly discussed herein.

The monitoring circuit 12 is typically coupled to the patient via two or more conventional ECG monitoring electrodes. As will be discussed in greater detail below, the monitoring circuit 12 includes the conventional processing circuitry required to sample, filter, and amplify electrical signals received from the different electrodes. The monitoring circuit 12 may further be constructed to produce, for example, any of the standard vectorcardiographic leads of ECG information from the received signals. The monitoring circuit 12 also typically includes some form of isolation circuitry designed to restrict the passage of potentially harmful currents between monitor circuit 12 and the patient.

The defibrillation circuit 14 conventionally includes some one or more capacitors used to store energy for discharge to the patient via the defibrillation paddles or electrodes. The amount of energy stored on the capacitor is controlled in response to inputs from the control and processing circuit 20. The energy is discharged by depressing discharge switches included on the defibrillation paddles or instrument. In a synchronized cardioversion mode of operation, the control and processing circuit 20 times the discharge to coincide with a particular portion of the cardiac cycle, identified using ECG information from the monitoring circuit 12.

Pacing circuit 16 is coupled to the patient via a pair of conventional pacing electrodes. The pacing circuit 16 is constructed to produce a periodic pulse of relatively low current used to initiate a desired heart rate in the patient. The magnitude and repetition rate of the pacing pulses are controlled by pacing circuit 16 in response to inputs from the control and processing circuit 20.

Figure 3:
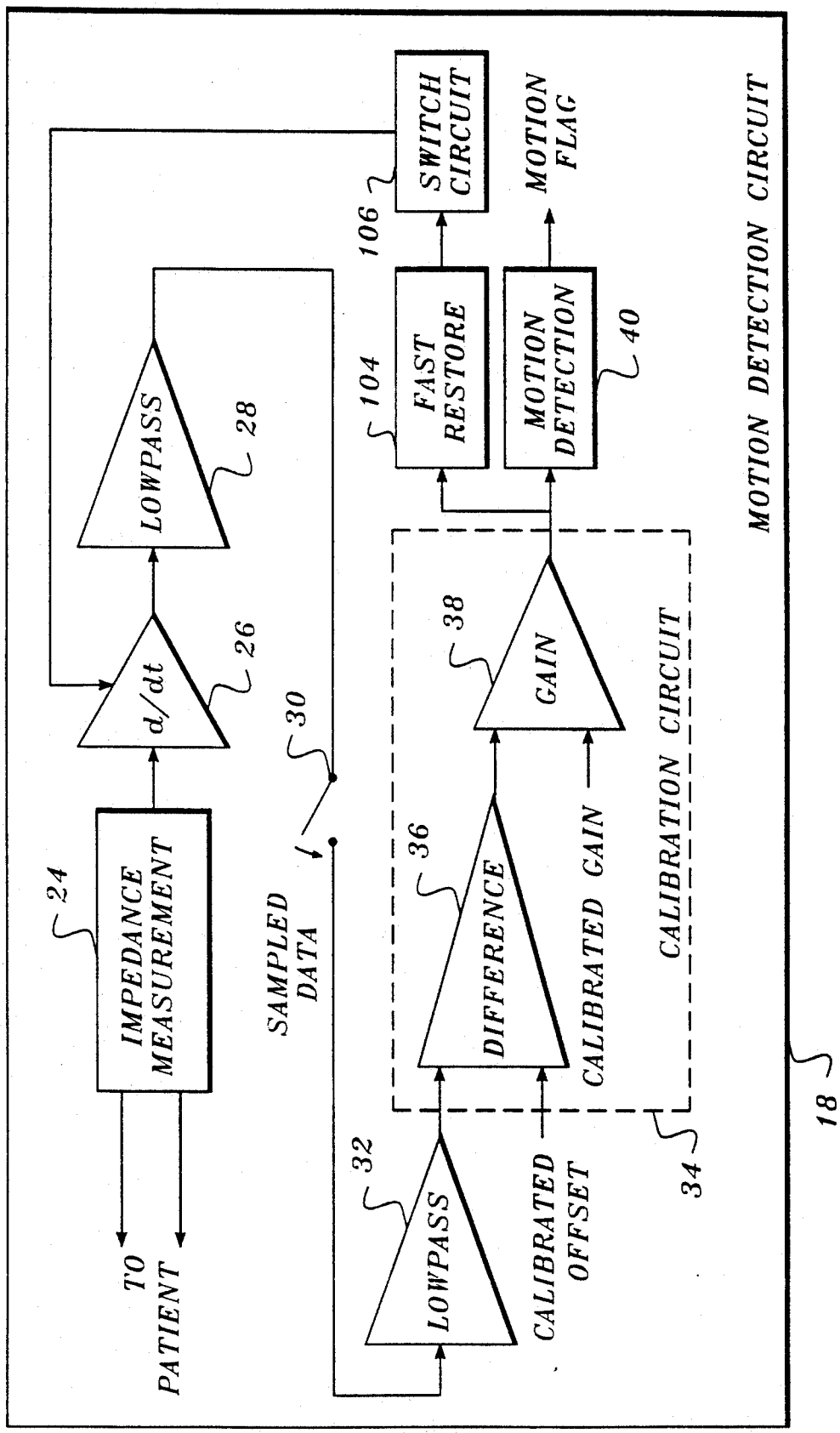
FIG. 3 is a more detailed block diagram of a motion detection circuit included in the defibrillator/monitor of FIG. 2.

Turning now to a discussion of the motion detection circuit 18, and the related operation of control and processing circuit 20, reference is had to FIG. 3. As shown, the motion detection circuit 18 includes a number of different components. In that regard, an impedance measurement circuit 24 is coupled to at least one pair of the various electrodes used with instrument 10.

In one currently preferred arrangement, motion of the patient relative to two monitoring electrodes is detected and used to indicate electrode/patient motion in general. As a result, the impedance measurement circuit 24 is coupled directly to two of the monitoring electrodes.

If desired, the impedance of one or more alternative sets of monitoring, defibrillation, or pacing electrodes can be evaluated to detect motion. In that regard, the control and processing circuit 20 could alternatively switch the connection of the impedance measurement circuit 24 to more than one electrode set, allowing a single circuit 24 to measure the impedance of various EGG, pacing, and/or defibrillation electrode pairs. As another option, a separate motion detection circuit 18 and, hence, impedance measurement circuit 24 could be connected to each of the different electrode pairs whose impedance is to be monitored.

The impedance measurement circuit 24 is of conventional construction, and generally involves the passage of a known current between a particular pair of electrodes of interest. The resultant voltage drop across the electrode pair is then representative of the collective impedance of the electrode pair, the patient, and the electrode/patient interfaces. Additional details regarding suitable impedance measurement circuits 24 can be obtained from the Marriott and Morgan et al. patents discussed above, the disclosures of which are incorporated by reference.

As previously suggested, the output of the impedance measurement circuit 24 is a time-varying voltage, measured using a 16 kiloHertz square wave. The magnitude of this voltage is proportional to the impedance of the electrodes, patient and electrode/patient interfaces. If the patient moves, the impedance of the electrode/patient interface will typically vary, causing the output of impedance measurement circuit 24 to vary accordingly.

As shown in FIG. 3, the output of the impedance measurement circuit 24 is applied to a differentiator 26. The differentiator 26 produces an output that is proportional to the derivative of, or change in, the impedance signal. As a result, although the output of differentiator 26 is still an impedance-based signal, the magnitude of the differentiated output is proportional to the motion detected, at least over short intervals. In the currently preferred embodiment, the differentiator 26 is, for example, a capacitive coupler between the impedance measurement circuit 24 and a low-pass filter 28.

As noted, the output of differentiator 26 is applied to a low-pass filter 28. The low-pass filter 28 may be of a Butterworth, or modified Butterworth, construction, which makes use of the capacitive nature of differentiator 26 and has a cut-off frequency of from one-to-ten Hertz. As will be appreciated, filter 28 thus removes extraneous high frequency components from the motion signal output by differentiator 26. These high frequency components may be attributable to, for example, radio frequency interference (rfi), static discharge interference, and cross talk within the electronics of instrument 10.

The next component of the motion detection circuit 18 shown in FIG. 3 is a sample and hold circuit 30. The sample and hold circuit 30 is used to repetitively sample and store the processed motion data from filter 28 for further processing. Circuit 30 may be, for example, a single-slope analog-to-digital (A/D) converter operated at 480 Hertz.

The information sampled by circuit 30 is then applied to a low-pass filter 32. Filter 32 is included to remove noise introduced into the conditioned motion signal by the sampling process. The low pass filter 32 may also be of the Butterworth type and has a cut-off frequency of roughly five Hertz.

In the present arrangement, the preceding components of circuit 18 have been described as being implemented with hardware. As described below, the remaining components are, in contrast, implemented in software. Alternative implementations can, of course, be employed.

The output from low-pass filter 32 is applied to a calibration circuit 34. The function of the calibration circuit 34 is to calibrate the filtered motion output so that it exhibits a predetermined or calibrated magnitude when no motion is present. In that regard, the calibration circuit 34 includes a differential amplifier 36 and variable gain amplifier 38.

The differential amplifier 36 has two inputs. One of these inputs is the filtered motion signal output by filter 32. The other input of amplifier 36 is a calibrated offset generated by the control and processing circuit 20. As a result, the output of differential amplifier 36 is effectively equal to the output of low pass filter 32 minus the offset. In the preferred arrangement, the appropriate offset is empirically determined during initialization of software used by the control and processing circuit 20. More particularly, with the electrodes coupled to a patient that is not moving, an automated calibration process executed by circuit 20 adjusts the offset until the output of amplifier 36 is equal to zero. In the currently preferred arrangement, amplifier 36 is implemented as a software difference operation.

The adjustable gain amplifier 38 next amplifies the output of amplifier 36 to ensure that the signal representative of motion has an amplitude that is sufficiently large to allow motion to be detected relatively easily and with the desired accuracy. In that regard, the amplifier 38 receives both the output of amplifier 36 and a gain input from the control and processing circuit 20. Like the offset, the magnitude of the gain input is empirically determined as part of an initialization process in which an automated calibration process executed by circuit 20 adjusts the gain to provide the desired performance over the range of expected motion. In the currently preferred arrangement, amplifier 38 is effectively provided by a controllable software gain factor.

Finally, the output of amplifier 38 is applied to a motion detection block 40 included in the motion detection circuit 18. Block 18 represents a sequence of operations performed by software included in the control and processing circuit 20. To illustrate the operation of the motion detection block 40, reference will be had to FIGS. 4 and 5, which further describe the construction and operation of the control and processing circuit 20.

Figure 4:
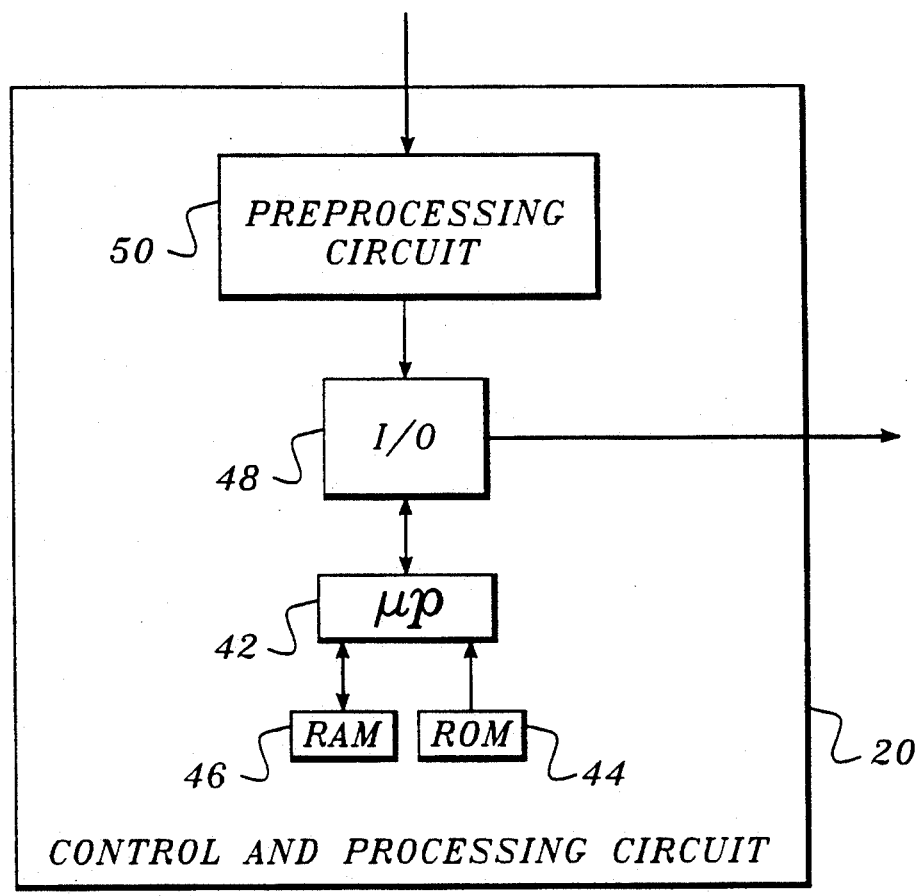
FIG. 4 is a more detailed block diagram of a control and processing circuit included in the defibrillator/monitor of FIG. 2.

In that regard, FIG. 4 is a block diagram of the control and processing circuit 20. As shown, the control and processing circuit 20 includes a microprocessor 42, which performs a variety of control and analysis operations determined by various software routines stored in a read only memory (ROM) 44. The microprocessor 42 stores information used in the control and analysis routines in a random access memory (RAM) 46. The microprocessor 42 is linked to the other components of the defibrillator/monitor 10 by an input/output (I/O) circuit 48 and a preprocessing circuit 50 which provide the necessary buffers and signal conversions required to allow microprocessor 42 to effectively interface with the remainder of the system.

Of the various software routines stored in ROM 44, one routine of particular interest is the motion detection routine 52 represented by the flow charts of FIGS. 5, 6, 7, and 10. As will be described in greater detail below, routine 52 monitors the processed motion signal from calibration circuit 34 and indicates that motion is occurring if that signal is outside a relatively large range for a short time or outside a smaller range for a longer time. The relationship of these two ranges and times gives motion detection routine 52 a hysteretic operation that reduces the influence of, for example, noise. As will be described in greater detail below, the relationship of the ranges and times used to determine the presence and, then, absence of motion can also be described as hysteretic in nature.

Figure 5:
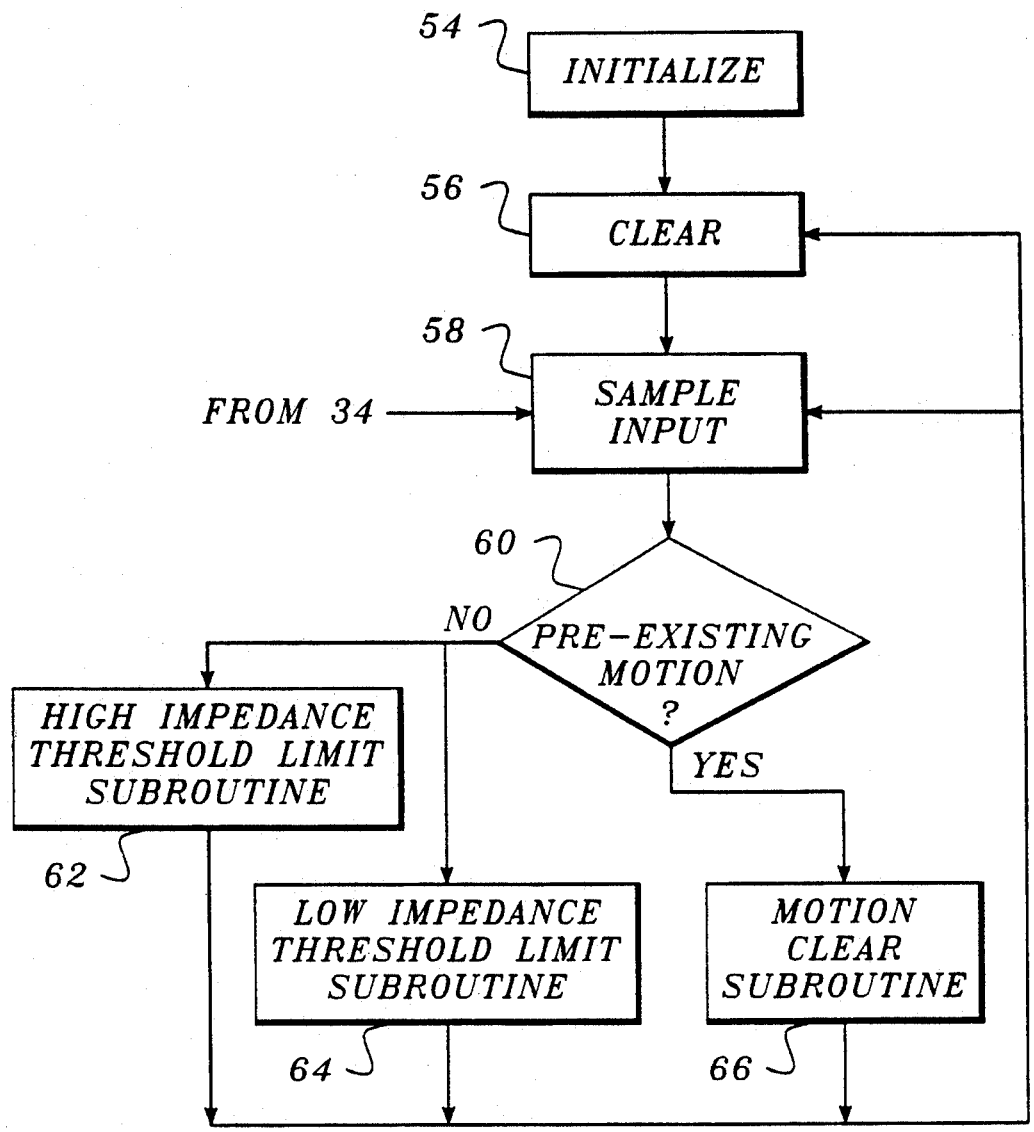
FIG. 5 is a flow chart illustrating the way in which the defibrillator/monitor processes an impedance signal to detect motion at the patient-electrode interface.
Figure 6:
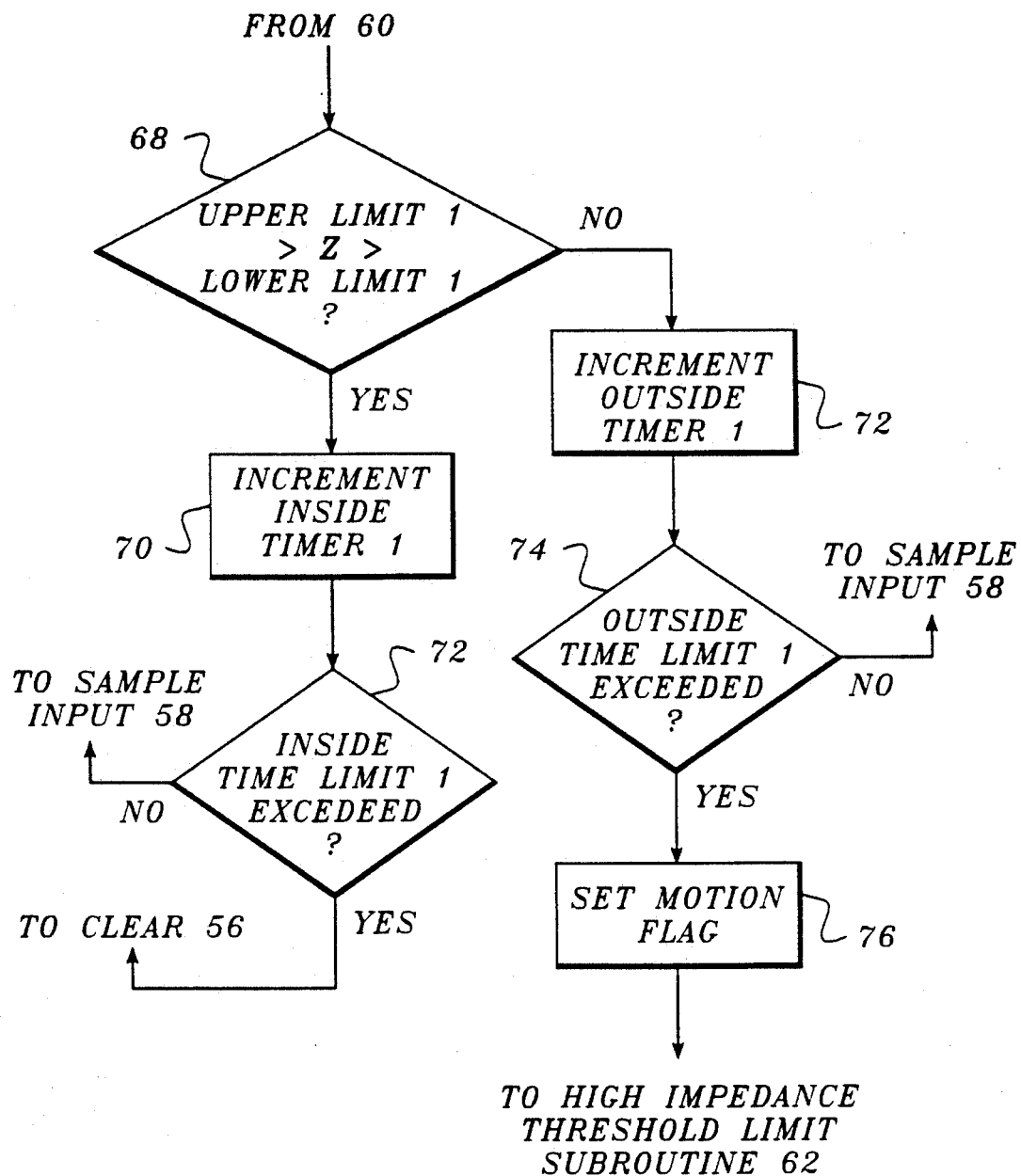
FIG. 6 is a more detailed flow chart, illustrating a high impedance threshold limit subroutine included in the flow chart of FIG. 5.

Once motion has been detected, routine 52 continues to indicate the presence of motion until the signal remains inside a relatively small range for a relatively long interval of time. Having briefly summarized the operation of motion detection routine 52, the routine will now be discussed in greater detail. As shown in FIG. 5, the routine 52 begins with an initialization step 54, in which the following parameters are initialized by microprocessor 42 to, for example, the following levels:

(1) upper limit 1 = +293 milliohms,
(2) lower limit 1 = −293 milliohms,
(3) inside time limit 1 = 33 milliseconds,
(4) outside time limit 1 = 100 milliseconds,
(5) inside procedure 1 = reset inside timer 1 and outside timer 1,
(6) outside procedure 1 = set motion flag,
(7) upper limit 2 = +117 milliohms,
(8) lower limit 2 = −117 milliohms,
(9) inside time limit 2 = 333 milliseconds,
(10) outside time limit 2 = 333 milliseconds,
(11) inside procedure 2 = reset inside timer 2 and outside timer 2,
(12) outside procedure 2 = set motion flag,
(13) upper limit 3 = +117 milliohm,
(14) lower limit 3 = −117 milliohm,
(15) inside time limit 3 = 1.50 seconds,
(16) outside time limit 3 = 750 milliseconds,
(17) inside procedure 3 = clear motion flag, and
(18) outside procedure 3 = reset inside timer 3 and outside timer 3.

For the purposes of the ensuing discussion, items (1)–(6) will be collectively referred to as condition group A, items (7)–(12) will be referred to as condition group B, and items (13)–(18) will be referred to as condition group C. These three groups of initialized parameters, which include both amplitude and time constraints, are used by routine 52 to hysteretically detect the presence of motion and the subsequent absence of motion.

After initialization, three inside timers 1, 2, and 3 and three outside timers 1, 2, and 3, employed by the routine, are cleared or set to zero at block 56. These timers are used to determine the length of time the signal from circuit 34 is within the various ranges of interest. Prepared in this manner, the routine 52 is now ready to start processing the output of the calibration circuit 34.

In that regard, the motion or impedance signal from circuit 34 is polled at block 58. At block 60, a test is performed to determine whether motion was detected during the last iteration of routine 52. In the event that motion was not detected, further operation of the motion detection routine 52 proceeds along a high impedance threshold limit subroutine 62 and a parallel low impedance threshold limit subroutine 64. Alternatively, if motion was previously detected, the operation of routine 52 proceeds via a motion clear subroutine 66.

Figure 8:
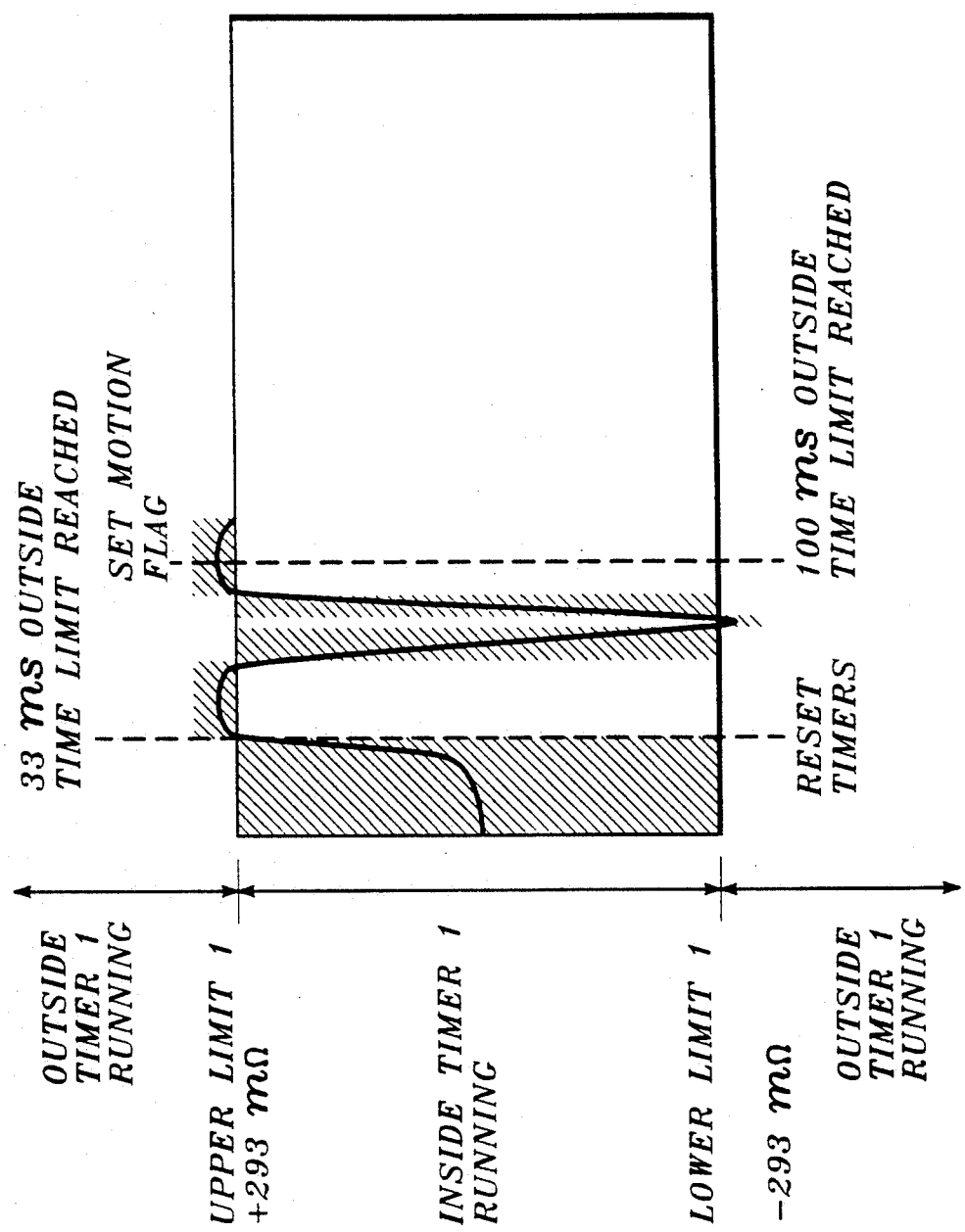
FIG. 8 is a graph depicting a time-varying signal processed by the defibrillator/monitor in accordance with the subroutine shown in FIG. 6, illustrating a pair of upper and lower limits used in the first part of a hysteretic motion detection operation performed by the instrument.

Reviewing these different subroutines individually, the relationship between the high impedance threshold limit subroutine 62 and the time-varying output of calibration circuit 34 is depicted graphically in FIG. 8. The subroutine 62 begins at block 68 where the impedance represented by the impedance-based motion signal is compared to the upper limit 1 and the lower limit 1. If the signal is between these limits, the inside timer is incremented at block 70. On the other hand, if the motion signal is outside those limits, the outside timer 1 is incremented at block 72.

If the inside timer 1 has been incremented at block 70, the present count on the inside timer 1 (representing the number of times the motion signal has fallen between upper limit 1 and lower limit 1) is compared to the inside time limit 1 at block 72. If the inside time limit 1 is exceeded, the inside and outside timers 1 are reset at block 56 and the cycle will then be repeated when the next input sample is sequentially received at block 58. On the other hand, if the inside time limit is not exceeded at block 70, operation is returned to block 58 for the receipt of the next input sample, without clearing of the timers.

Alternatively, if the outside timer 1 has been incremented at block 72, the present count on the outside timer 1 (representing the number of times the motion signal has fallen outside the range defined by upper limit 1 and lower limit 1) is compared to the outside time limit 1 at block 74. If the outside time limit 1 has been exceeded, a motion flag is set at block 76. On the other hand, if the outside time limit 1 has not been exceeded, the next input sample is obtained at block 58.

As will be appreciated, the basic flow of the high impedance subroutine 62 is repeated for each new sample obtained at block 58 until the motion flag is finally set at block 76 by either the high impedance subroutine 62, or the low impedance subroutine 64 described next.

Figure 7:
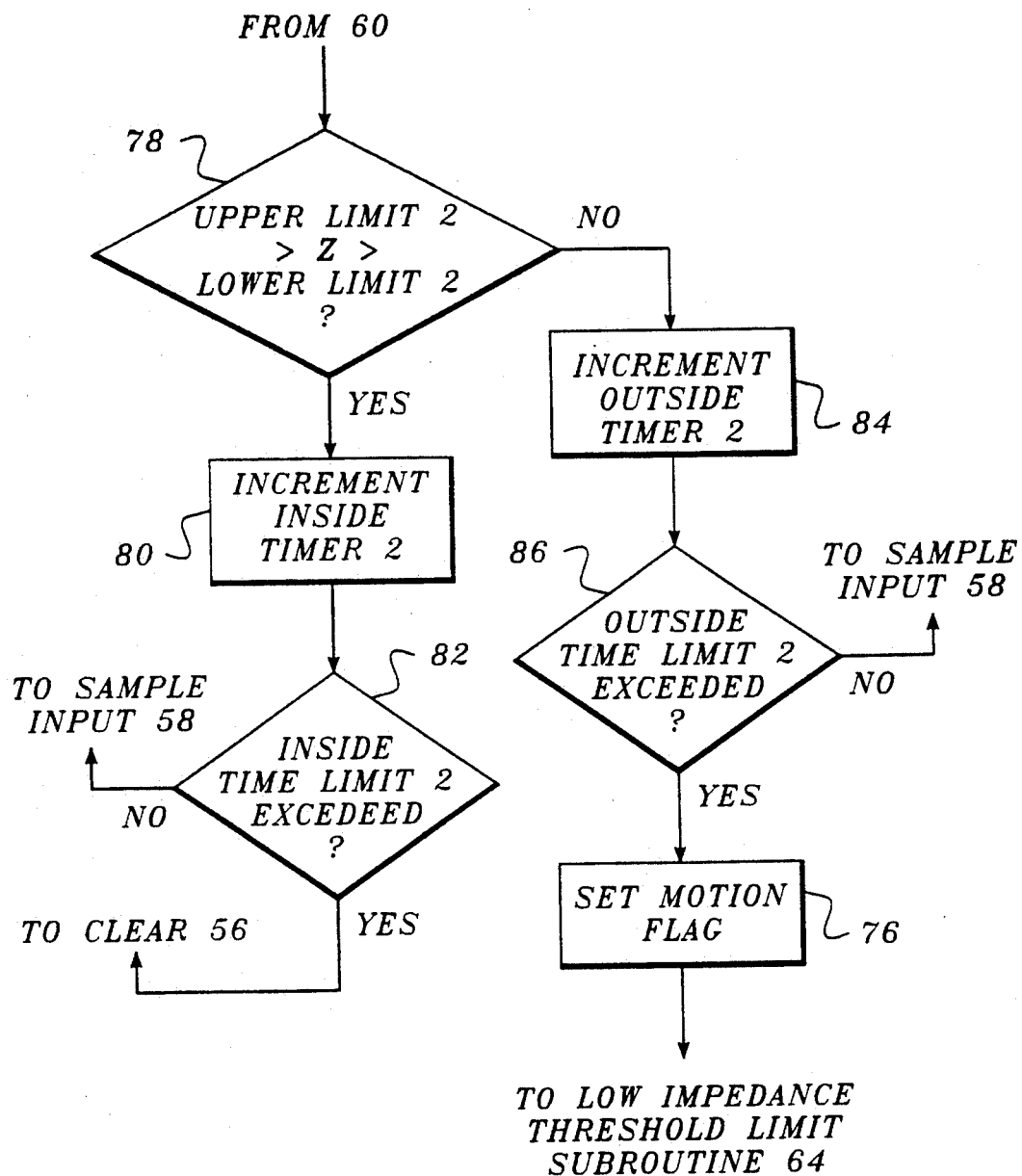
FIG. 7 is a more detailed flow chart, illustrating a low impedance threshold limit subroutine included in the flow chart of FIG. 5.
Figure 9:
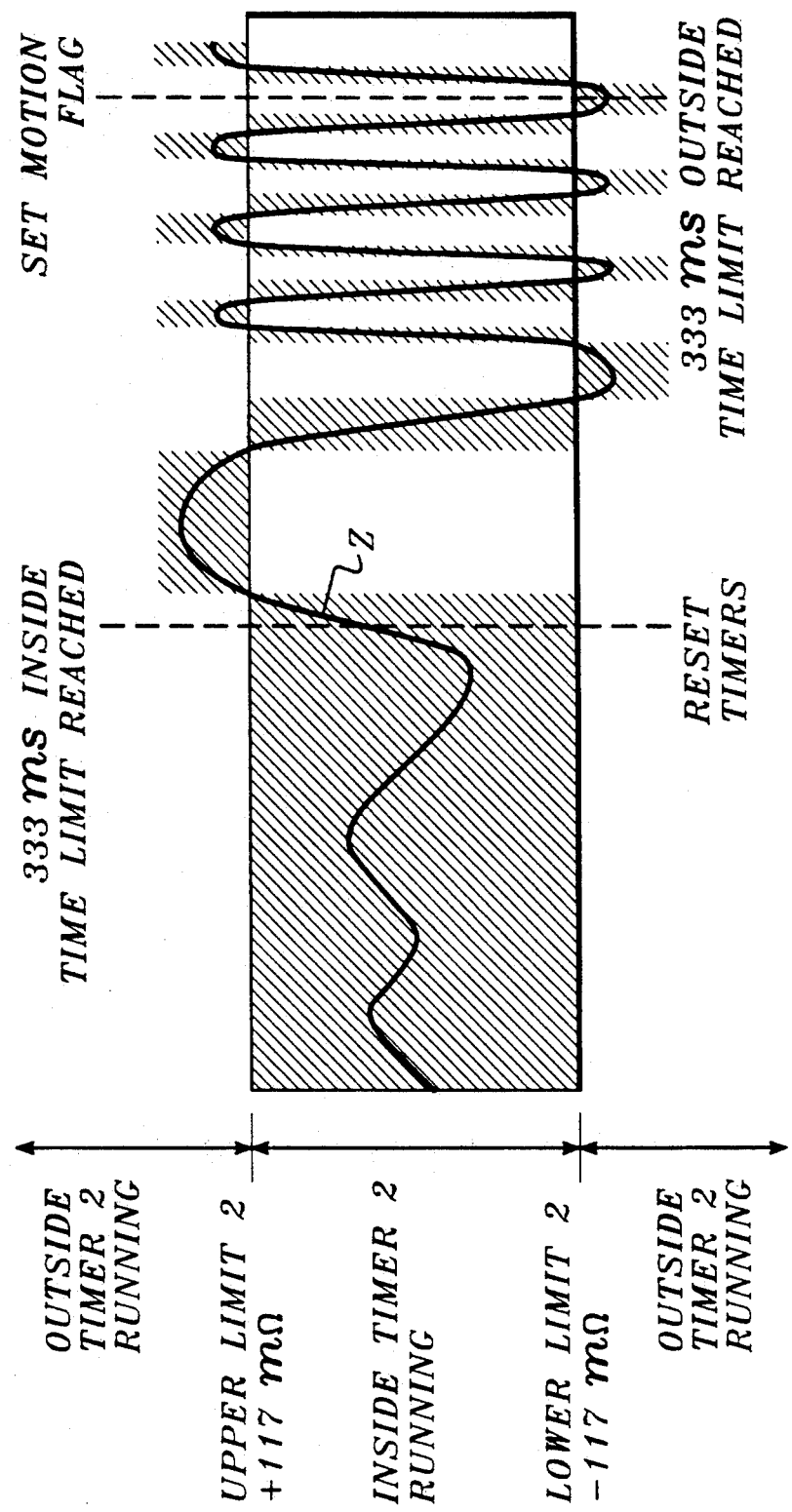
FIG. 9 is a graph depicting a time-varying signal processed by the defibrillator/monitor in accordance with the subroutine shown in FIG. 7, illustrating a pair of upper and lower limits used in the second part of a hysteretic motion detection operation performed by the instrument.

In that regard, the low impedance subroutine 64 is shown in FIG. 7 and its relationship to the output of circuit 34 is graphically depicted in FIG. 9. At the same time an input sample is applied to block 68 of subroutine 62, the sample is also applied to another block 78 in subroutine 64. At block 78, the motion signal is compared to an upper limit 2 and lower limit 2. In the event a particular input sample falls between these limits, the inside timer 2 is incremented at block 80 and a test is performed at block 82 to determine whether the inside time limit 2 has been exceeded. In the event that it has, the inside and outside timers 2 are cleared at block 56. If inside time limit 2 has not been exceeded, a new input sample is obtained at block 58.

On the other hand, if the input sample is outside the range defined by upper limit 2 and lower limit 2, the outside timer 2 is incremented at block 84. A test is then performed at block 86 to determine whether the outside time limit 2 has been exceeded. In the event the outside time limit 2 has been exceeded, a motion flag is set at block 76. Alternatively, if the outside time limit 2 has not been exceeded, the inside and outside timers 2 are cleared at block 56.

The high and low impedance subroutines 62 and 64 cooperatively check the input for relatively large variations over short times and smaller variations over longer times. This hysteretic analysis is relatively unsusceptible to the influence of, for example, noise because it is unlikely that (1) the magnitude of the noise would be sufficient to cause the input to exceed the larger range limits, or (2) the recurrence of the noise would be sufficient to cause the input to exceed the smaller range limits for the longer time. As will be appreciated, if subroutine 62 were used by itself, a signal representative of moderate but continuous motion might not exceed the range limits for the short duration involved. Similarly, it subroutine 64 were used by itself, a signal representative of substantial but brief motion might not exceed the lower range limits for a sufficiently long time.

Expressed in another way, the subroutines 62 and 64 rely upon different condition groups A and B to detect motion. Condition group A is used to reduce the influence of channel saturation on the detection of motion, while condition group B is used to reduce the influence of low level motion noise on the detection of motion. The combined use of the condition groups with their different amplitude and time constraints gives the routine 52 a characteristic operation referred to herein as hysteretic.

With the motion flag set at block 76 by either subroutine 62 or 64, an output would normally be applied to the defibrillation circuit 14 to inhibit the discharge of energy to the patient. As a result, a moving patient can not be defibrillated, protecting both the patient and any attending health care provider that might be moving the patient. If desired, the motion flag may also be used to, for example, alert the operator to potential errors in the information collected by monitoring circuit 12.

Figure 10:
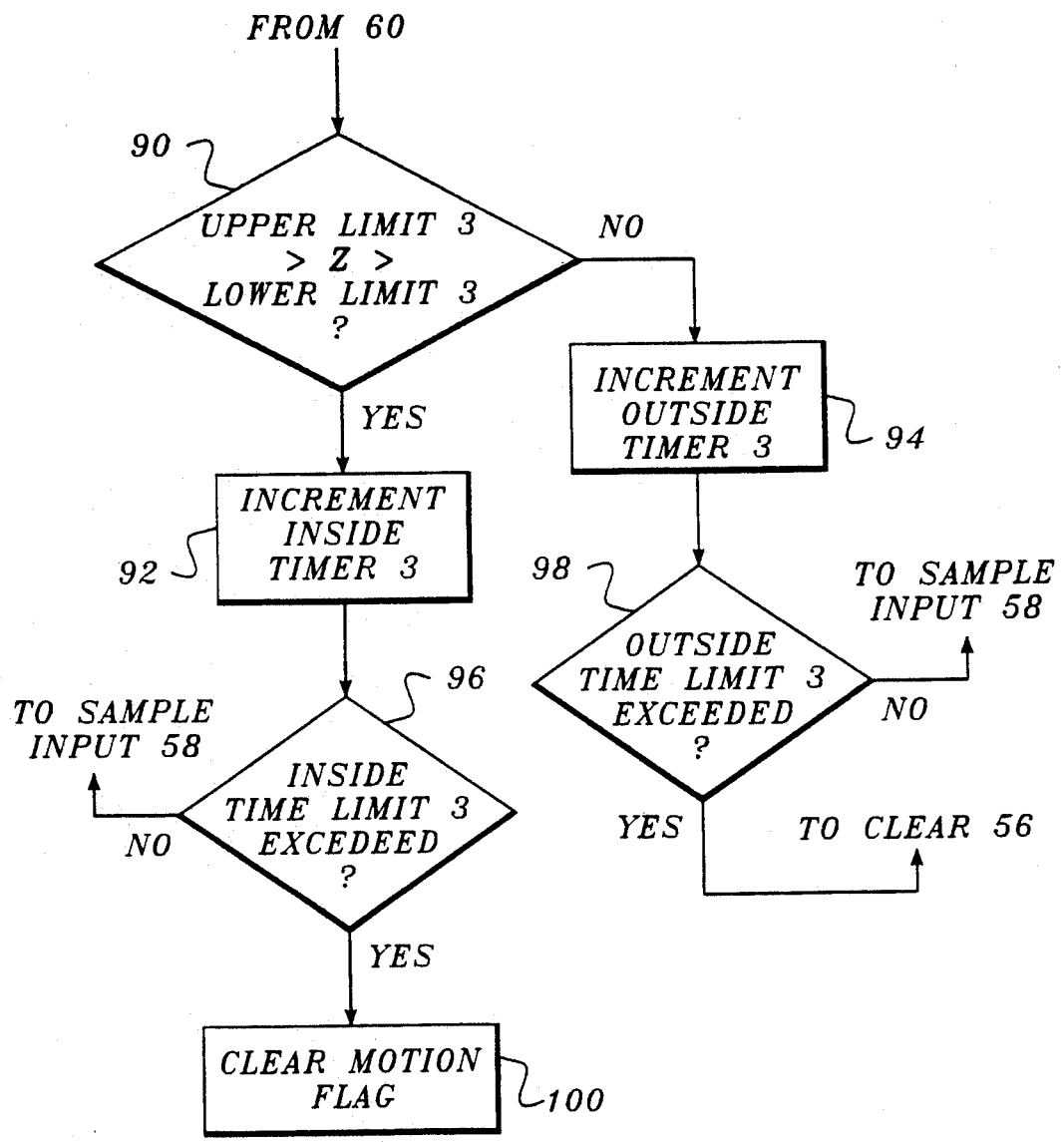
FIG. 10 is a flow chart illustrating a motion clear subroutine included in the flow chart of FIG. 5 and used by the defibrillator/monitor to determine when motion is no longer present.
Figure 11:
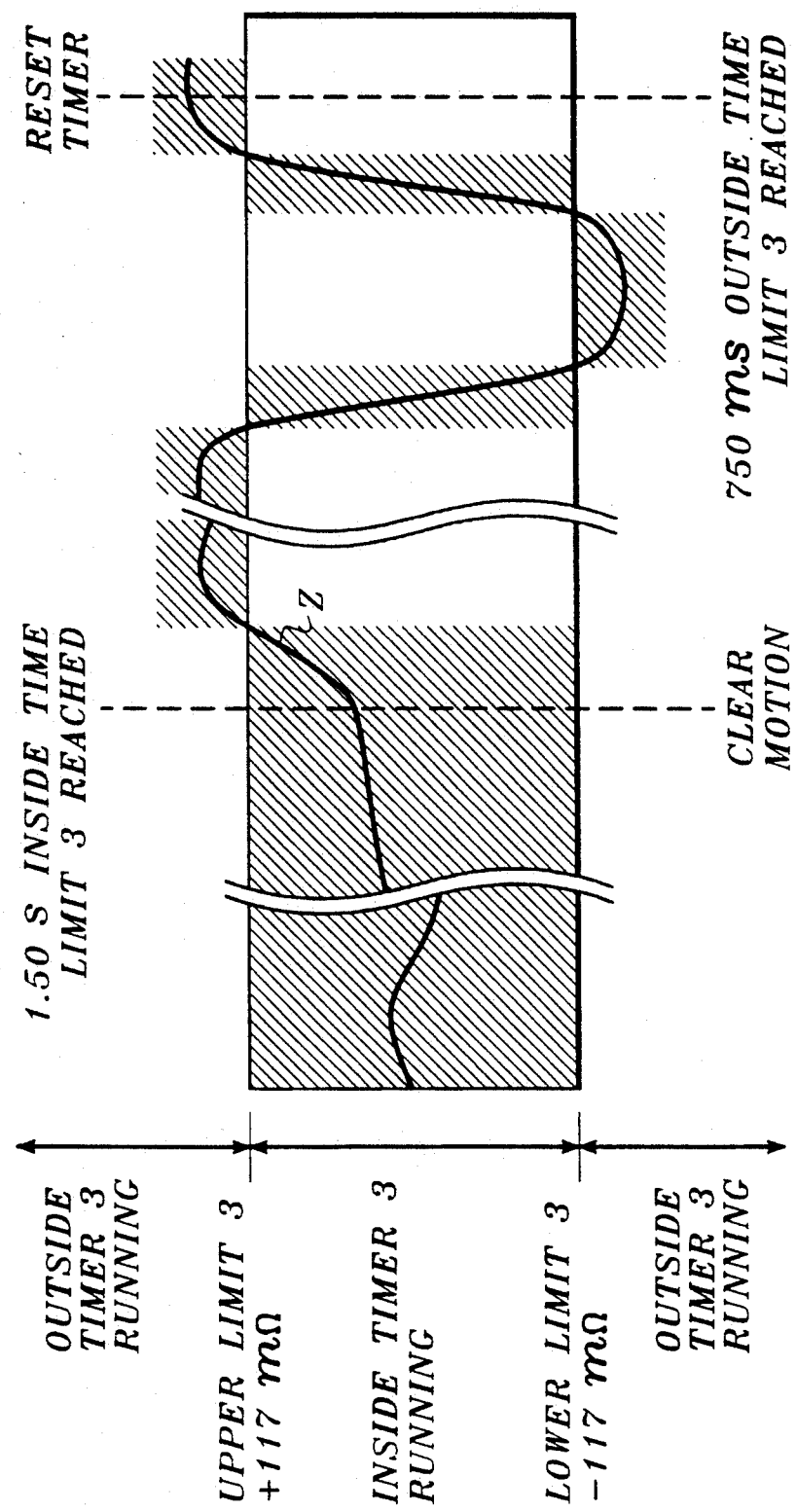
FIG. 11 is a graph depicting a time-varying signal processed by the defibrillator/monitor in accordance with the subroutine shown in FIG. 10.

Once the motion flag has been set at block 76, the motion detection routine 52 continues via the motion clear subroutine 66 depicted in FIG. 10. The relationship of the processed motion signal to the various parameters employed by this portion of routine 52 is depicted graphically in FIG. 11.

As shown in FIG. 10, with block 60 having determined that the motion flag is set, the input sample is compared to upper limit 3 and lower limit 3 at block 90. In the event that the sample is between upper limit 3 and lower limit 3, the inside timer 3 is incremented at block 92. Alternatively, if the sample obtained at block 88 is outside the range defined by upper limit 3 and lower limit 3, the outside timer 3 is incremented at block 94.

At blocks 96 and 98 tests are performed to determine whether the inside time limit 3 and outside time limit 3 have been exceeded, respectively. In the event the inside time limit 3 has been exceeded, the motion flag is cleared at block 100. On the other hand, if inside time limit 3 has not been exceeded at block 96, the routine returns to block 58 to obtain the next sample of the motion signal. If block 98 determines that the outside time limit 3 has been exceeded, the inside timer 3 and outside timer 3 are reset at block 56 and the next input sample is obtained at block 58. On the other hand, if the outside time limit 3 has not been exceeded at block 98, the next input sample is obtained without clearing the timers.

As noted above, the combined use of subroutines 62 and 64 (employing condition groups A and B) in the detection of motion, causes the motion detection routine 52 to operate in a hysteretic manner while detecting motion. Similarly, the combined use of subroutine 62 (employing condition group A) to detect motion and subroutine 66 (employing condition group C) to clear the motion flag, or the combined use of subroutine 64 (employing condition group B) to detect motion and subroutine 66 (employing condition group C) to clear the motion flag, causes the motion detection routine 52 to operate in a hysteretic manner while setting and clearing a motion flag. In both cases, the operations involve separate amplitude and time limits, which may be related in substantially any manner desired.

As will also be appreciated, any one of the three different subroutines of the motion detection routine 52 represent a basic protocol whose applicability in the instrument is not limited solely to motion detection. For example, it may be helpful to compare a variety of different physiological signals processed by the instrument to some range defined by upper and lower limits. If the input is within the range, an inside timer is incremented and, when the inside timer exceeds the inside time limit, some inside procedure is performed. Alternatively, if the input is outside the range, an outside timer is incremented and an outside procedure performed when the outside timer is greater than the outside time limit. If this process is performed for different ranges and/or times a hysteretic aspect is introduced into the analysis.

Figure 12:
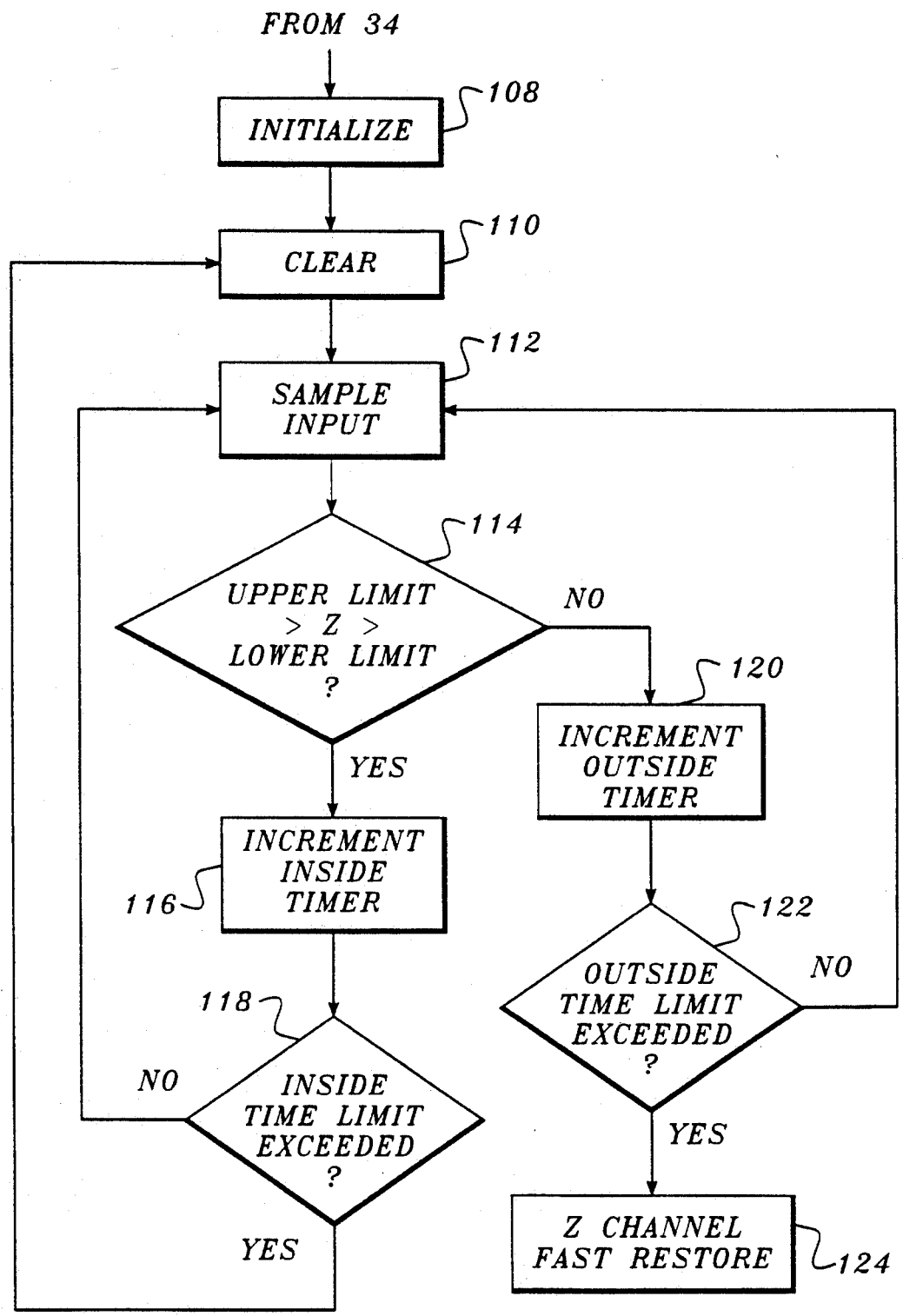
FIG. 12 is a flow chart illustrating the way in which the defibrillator/monitor processes impedance signals to activate a fast-restoration system included in the motion detection circuit of FIG. 3.

One alternative application for such a protocol is a fast restore routine 102, shown in FIG. 12. The fast restore routine 102 can be used in the motion detection circuit 18 of FIG. 3, where it is represented by block 104. The routine 102 is used to determine when deviations in the input signal are so great as to fully charge the capacitive coupling of the differentiator 26 connected to filter 28, rendering the filter inoperative. In that case, an output from the fast restore block 104 is applied to a switch circuit 106 to temporarily close a switch or switches coupled in parallel to the differentiator capacitance. As a result, the energy stored by the differentiator 26 is quickly discharged and, when the switches in circuit 106 are again opened, the filter and motion detection circuit 18 are restored to operability.

Reviewing the operation of the fast restore routine 102 in greater detail, at block 108, the upper and lower limits are established at, for example, +one ohm and −one ohm. The inside and outside times are established at, for example, 83 milliseconds and 330 milliseconds, respectively. At block 110, the inside timer and outside timer are cleared.

Next, the signal from calibration circuit 34 is sampled at block 112. At block 114, the impedance represented by the input signal sample is compared to the upper and lower limits. In the event that this impedance is inside the range defined by the upper and lower limits, the inside timer is incremented at 116. Then a test is performed at block 118 to determine whether the inside time limit has been exceeded. If the inside time limit has been exceeded, the timers are reset at block 110 prior to the collection of the next signal sample at block 112. Alternatively, if the inside timer limit has not been exceeded, the next signal sample is obtained at block 112 without resetting the timers.

On the other hand, if block 114 determines that the impedance of the signal sample is outside the range defined by the upper and lower limits, the outside timer is incremented at block 120. A test is then performed at block 122 to determine whether the outside time limit has been exceeded. If the outside time limit has not been exceeded, the next input sample is obtained at block 112.

On the other hand, if the outside time limit has been exceeded, an impedance channel fast restore flag is set at block 124. With the upper and lower limits and outside time limit set appropriately, the fast restore flag will thus be set when an unacceptably severe deviation has occurred in the input signal, fully charging the differentiator capacitance and rendering filter 28 inoperative.

As noted previously, the impedance channel fast restore output from block 124 is applied to a shunting switch or switches included in switch circuit 106. These switches are connected in parallel with the capacitance associated with differentiator 26 and filter 28 of the motion detection circuit 18 shown in FIG. 3. The fast restore output initially closes the switches, discharging the energy stored by the capacitances to ground. Once the energy has been discharged, the switches are opened, having restored filter 28 and circuit 18 to their operative condition.

Although not described in the same level of detail, it will be appreciated that the basic fast restore routine 102 of FIG. 12 can also be used advantageously in other filter circuits, including those in the ECG monitor circuit 12 of FIG. 2. In that regard, an ECG processing section of the monitor circuit 12 can be constructed to closely parallel the motion detection circuit 18 of FIG. 3. The primary differences between the two circuits are as follows.

As will be appreciated, the ECG processing circuit includes an ECG measurement circuit in place of the impedance measurement circuit 24. The output of the ECG measurement circuit is proportional to one lead of the ECG information obtained from the patient. In addition, as will be appreciated, the differentiator 26 and motion detection block 40 of motion detection circuit 18 are not required and are, therefore, absent from the ECG processing circuit. Otherwise, the processing circuit and motion detection circuit 18 are the same.

Regarding the use of fast restore routine 102 with monitor circuit 12, as might be expected, the various parameters initialized at block 108 will be different than those previously discussed in connection with the motion detection circuit 18. More particularly, the upper and lower limits are initialized at +5.5 and −5.5 millivolts, the outside time limit is set at 67 milliseconds, and the inside time limit is set at 33 milliseconds.

The analysis performed by routine 102 using these various limits then follows that discussed above. It should be noted, however, that the test performed at block 114 involves a comparison of the ECG-based, rather than impedance-based, output of calibration circuit 34 and the flag set at block 124 in an ECG channel fast restore, rather than impedance channel fast restore. Ultimately, the ECG channel fast restore flag is used to close the switches in switch circuit 106 and restore filter 28 to operability.

Those skilled in the art will recognize that the embodiments of the invention disclosed herein are exemplary in nature and that various changes can be made therein without departing from the scope and the spirit of the invention. In that regard, as was suggested above, various combinations of range and/or time limits can be used. For example, while one or two evaluations involving both range and time limits may be employed, alternative evaluations involving only range or time limits may be used. Because of the above and numerous other variations and modifications that will occur to those skilled in the art, the following claims should not be limited to the embodiments illustrated and discussed herein.

The embodiments of the invention in which an exclusive property or privilege is claimed are defined as follows:

1. A method of detecting relative motion between an electrode and a patient, the electrode being coupled to the patient and to a medical instrument, the instrument providing a signal related to the impedance of the electrode/patient interface, said method comprising the steps of:
   (a) comparing the signal to a first range of values;
   (b) storing a first inside time representative of the time during which the signal is within the first range of values and a first outside time representative of the time during which the signal is outside the first range of values;
   (c) setting the first inside and outside times to zero when the first inside time exceeds a first inside time limit; and
   (d) producing a motion detection output indicative of relative motion between the electrode and the patient when the first outside time exceeds a first outside time limit.

2. The method of claim 1, further comprising the steps of:
   comparing the signal to a second range of values;
   storing a second inside time representative of the time during which the signal is within the second range of values and a second outside time representative of the time during which the signal is outside the second range of values;
   setting the second inside and outside times to zero when the second inside time exceeds a second inside time limit;
   producing a motion detection output representative of relative motion between the electrode and the patient when the second outside time exceeds a second outside time limit.

3. The method of claim 2, further comprising the steps of:
   comparing the signal to a third range of values;
   storing a third inside time representative of the time during which the signal is within the third range of values and a third outside time representative of the time during which the signal is outside the third range of values;
   setting the third inside and outside times equal to zero when the third outside time exceeds a third outside time limit; and
   disabling a previously produced motion detection output when the third inside time exceeds a third inside time limit.

4. The method of claim 3, wherein first range of values roughly extends from −0.293 ohm to +0.293 ohm, the first inside time limit is roughly equal to 0.033 second, the first outside time limit is roughly equal to 0.100 second, the second range of values roughly extends from −0.117 ohm to +0.117 ohm, the second inside time limit is roughly equal to 0.333 second, the second outside time limit is roughly equal to 0.333 second, the third range of values roughly extends from −0.117 ohm to +0.117 ohm, the third inside time limit is roughly equal to 1.5 seconds, and the third outside time limit is roughly equal to 0.750 second.

5. A system for use with an instrument in detecting motion between a patient and an electrode, the electrode being couplable to the patient and the instrument, said system comprising:
   impedance detection means for producing a signal representative of the impedance between the electrode and the patient;
   comparator means for producing a first output indicative of whether the signal is within a first impedance range;
   timer means for monitoring the first output to produce a first inside signal representative of an interval of time the signal is inside the first impedance range and a first outside signal representative of an interval of time the signal is outside the first impedance range;
   reset means for setting the first inside and outside signals to zero when the first inside signal exceeds a first inside time limit; and
   motion detection means for producing a motion detection output indicative of relative motion between the electrode and the patient when the first outside signal ecceeds a first outside time limit.

6. The system of claim 5, wherein:
   said comparator means is further for producing a second output indicative of whether the signal is within a second impedance range;
   said timer means is further for monitoring the second output to produce a second inside signal representative of an interval of time the signal is inside the second impedance range and a second outside signal representative of an interval of time the signal is outside the second impedance range;
   said reset means is further for setting the second inside and outside signals to zero when the second inside signal exceeds a second inside time limit; and
   said motion detection means is further for producing a motion detection output indicative of relative motion between the electrode and the patient when the second outside signal exceeds a second outside time limit.

7. The system of claim 6, wherein:
   said comparator means is further for producing a third output indicative of whether the signal is within a third impedance range;
   said timer means is further for monitoring the third output to produce a third inside signal representative of an interval of time the signal is inside the third impedance range and a third outside signal representative of an interval of time the signal is outside the third impedance range;
   said reset means if further for setting the third inside and outside signals to zero when the third outside signal exceeds a third outside time limit; and
   further comprising disablement means for disabling a previously produced motion detection output when the third inside signal exceeds a third inside time limit.

8. A limit detection system for use in a medical instrument to analyze a signal that is related to a patient parameter, said limit detection system comprising:
   threshold means for comparing the signal to a first range of values;
   inside timer means for storing an indication of a first inside time during which the signal is within the first range of values;
   inside procedure means for instructing the instrument to initiate a first inside procedure when the first inside time exceeds a first inside time limit;
   outside timer means for storing an indication of a first outside time during which the signal is outside the first range of values; and
   outside procedure means for instructing the instrument to initiate an procedure when the first outside time exceeds a first outside time limit.

9. The system of claim 8, wherein said threshold means is further for comparing the signal to a second range of values, said inside timer means is further for storing an indication of a second inside time during which the signal is within the second range of values, said inside procedure means is further for instructing the instrument to initiate a second inside procedure when the second inside time exceeds a second inside time limit, said outside timer means is further for storing an indication of a second outside time during which the signal is outside the second range of values, and said outside procedure means is further for instructing the instrument to initiate a second outside procedure when the second outside time exceeds a second outside time limit.

10. The system of claim 9, wherein the signal is representative of the impedance between an electrode, coupled to the instrument, and a patient.

11. The system of claim 10, wherein said inside procedure means comprises reset means for resetting the inside and outside times to zero and wherein said outside procedure means comprises motion detection means for providing a motion detection output to the instrument indicative of relative motion between the electrode and patient.

12. The system of claim 8, wherein the signal is representative of the impedance between an electrode, coupled to the instrument, and a patient.

13. The system of claim 12, wherein said inside procedure means comprises reset means for resetting the inside and outside timers to zero and wherein said outside procedure means comprises fast restore means for providing a fast restore output to the instrument indicative of an undesired disturbance in the signal.

14. The system of claim 8, wherein the signal is representative of an electrocardiographic signal received by the instrument.

15. The system of claim 14, wherein said inside procedure means comprises reset means for resetting the inside and outside timers to zero and wherein said outside procedure means comprises fast restore means for providing a fast restore output to the instrument indicative of an undesired disturbance in the signal.

16. A method of detecting the limits of a physiological signal processed by a medical instrument comprising the steps of:
(a) comparing the signal to a first range of values;
(b) storing an inside time, representative of the time during which the signal is substantially within the range of values, and an outside time, representative of the time during which the signal is substantially outside the range of values;
(c) producing an inside action signal when the inside time exceeds a first inside time limit and an outside action signal when the outside time exceeds a first outside time limit; and
(d) repeating steps (a) through (c) for a second range of values.

17. The method of claim 16, wherein the step of repeating step (c) comprises the step of producing an inside action signal when the inside time exceeds a second inside time limit and an outside action signal when the outside time exceeds a second outside time limit.

18. The method of claim 17, wherein the first and second ranges of values are different, the first and second inside time limits are different, and the first and second outside time limits are different.

19. The method of claim 16, wherein a condition of interest may be associated with the physiological signal and the inside action signal produced during the initial performance of step (c) or the repetition of step (c) is used to detect the condition of interest.

20. The method of claim 16, wherein a condition of interest may be associated with the physiological signal, the inside action signal produced during the initial performance of step (c) is used to detect the presence of the condition of interest, and the inside action signal produced during the repetition of step (c) is used to detect the absence of the condition of interest.

21. A method of restoring a filter circuit used to process a physiological signal to a medical instrument comprising the steps of:
(a) comparing the signal to a first range of values;
(b) storing a first inside time representative of the time during which the signal is within the first range of values and a first outside time representative of the time during which the signal is outside the first range of values;
(c) setting the first inside time and outside times to zero when the first inside time exceeds a first inside time limit;
(d) producing a fast restore output indicative of excessive charging of the filter circuit when the first outside time exceeds a first outside time limit.

22. A method of detecting relative motion between an electrode and a patient and restoring a filter circuit employed in the detection of motion, the electrode being coupled to the patient and to a medical instrument including the filter circuit, the instrument providing a signal related to the impedance of the electrode/patient interface, said method comprising the steps of:
(a) comparing the signal to a first range of values;
(b) storing a first inside time representative of the time during which the signal is within the first range of values and a first outside time representative of the time during which the signal is outside the first range of values;
(c) setting the first inside and outside times to zero when the first inside time exceeds a first inside time limit;
(d) producing a motion detection output indicative of relative motion between the electrode and the patient when the first outside time exceeds a first outside time limit;
(e) comparing the signal to a second range of values;
(f) storing a second inside time representative of the time during which the signal is within the second range of values and a second outside time representative of the time during which the signal is outside the second range of values;
(g) setting the second inside and outside times to zero when the second inside time exceeds a second inside time limit; and
(h) producing a fast restore output indicative of excessive charging of the filter circuit when the second outside time exceeds a second outside time limit.

23. The method of claim 22, further comprising the steps of:
comparing the signal to a third range of values;
storing a third inside time representative of the time during which the signal is within the third range of values and a third outside time representative of the time during which the signal is outside the third range of values;
setting the third inside and outside times to zero when the third inside time exceeds a third inside time limit; and
producing a motion detection output indicative of relative motion between the electrode and the patient when the third outside time exceeds a third outside time limit.

* * * * *